(12) United States Patent
Kosecoff

(10) Patent No.: US 11,544,876 B2
(45) Date of Patent: Jan. 3, 2023

(54) INTEGRATED COSMETIC DESIGN APPLICATOR

(71) Applicant: L'Oreal, San Francisco, CA (US)

(72) Inventor: David B. Kosecoff, San Francisco, CA (US)

(73) Assignee: L'OREAL, Paris (FR)

( * ) Notice: Subject to any disclaimer, the term of this patent is extended or adjusted under 35 U.S.C. 154(b) by 61 days.

(21) Appl. No.: 17/246,355

(22) Filed: Apr. 30, 2021

(65) Prior Publication Data

US 2022/0351414 A1 Nov. 3, 2022

(51) Int. Cl.
*G06T 7/90* (2017.01)
*A61K 8/70* (2006.01)
*A61Q 1/02* (2006.01)

(52) U.S. Cl.
CPC .................. *G06T 7/90* (2017.01); *A61K 8/70* (2013.01); *A61Q 1/02* (2013.01); *A61K 2800/438* (2013.01); *G06T 2207/10024* (2013.01); *G06T 2207/30201* (2013.01)

(58) Field of Classification Search
CPC .............. G06T 7/90; G06T 2207/0024; G06T 2207/30201; A61K 8/70; A61K 2800/438; A61Q 1/02
USPC .......................................................... 382/162
See application file for complete search history.

(56) References Cited

U.S. PATENT DOCUMENTS 10,324,739 B2 * 6/2019 Chou .................... G06T 11/001
2003/0041871 A1 3/2003 Endo et al.
2012/0017929 A1 1/2012 Samain et al.
2012/0024308 A1 2/2012 Giron et al.
2013/0247928 A1 * 9/2013 Valucci .................. A45D 44/12
132/319

(Continued)

FOREIGN PATENT DOCUMENTS

CN 108402643 A 8/2018
CN 109671142 A 4/2019

(Continued)

OTHER PUBLICATIONS

International Search Report and Written Opinion, dated Jul. 18, 2022, in corresponding International Patent Application No. PCT/US2022/026751, 13 pages.

(Continued)

*Primary Examiner* — Gabriel I Garcia
(74) *Attorney, Agent, or Firm* — Christensen O'Connor Johnson Kindness PLLC

(57) ABSTRACT

Systems and methods for application of cosmetic designs are described. In an embodiment, the system includes a visible light mirror, comprising a first portion being at least partially transparent to visible light; a camera, optically coupled with the visible light mirror to receive visible light via the first portion; an illumination source, physically coupled with the visible light mirror and configured to emit a plurality of discrete wavelength channels; and a computer system, electronically coupled with the camera and the illumination source, and comprising one or more processors and a non-transitory computer readable storage medium storing instructions that, when executed by the one or more processors, cause the one or more processors to perform one or more methods of the present disclosure.

15 Claims, 7 Drawing Sheets

(56) References Cited

U.S. PATENT DOCUMENTS

2016/0374453 A1* 12/2016 Maruyama ............. A45D 40/20
                                                          401/192
2018/0037116 A1*  2/2018 Avery ................... B60K 35/00

FOREIGN PATENT DOCUMENTS

| EP | 3709638 A1 | 9/2020 |
| WO | 2010095118 A2 | 8/2020 |

OTHER PUBLICATIONS

Jin et al., Photo-Chromeleon: Re-Programmable Multi-Color Textures using Photochromic Dyes, HCI Engineering, MIT C SAIL, 2019.

* cited by examiner

INTEGRATED COSMETIC DESIGN APPLICATOR

SUMMARY

Methods, systems, and devices for integrated photochromic cosmetic application are described. In one aspect, a system for application of cosmetic designs, the system includes a visible light mirror, includes a first portion being at least partially transparent to visible light. The system also includes a camera, optically coupled with the visible light mirror to receive visible light via the first portion. The system also includes an illumination source, physically coupled with the visible light mirror and configured to emit a plurality of discrete wavelength channels. The system also includes a computer system, electronically coupled with the camera and the illumination source, and includes one or more processors and a non-transitory computer readable storage medium storing instructions that, when executed by the one or more processors, cause the one or more processors to perform operations including receiving a numerical representation of a cosmetic design, including a tensor of color intensity information for a plurality of colors, the plurality of colors corresponding to a photochromatic formulation includes a mixture of photochromic materials, detecting a user of the system facing the visible light mirror, generating a numerical representation of a portion of a face of the user using the camera, the numerical representation of the face includes a tensor of position information defining a surface of the face, defining an exposure pattern for the surface of the face, at least in part by projecting the tensor of color intensity information onto the tensor of position information, and exposing the surface of the face with the plurality of discrete wavelength channels in accordance with the exposure pattern using the illumination source.

The camera may include multiple image sensors, configured to capture stereoscopic images.

The illumination source may be optically coupled with the visible light mirror at a second portion of the visible light mirror, and where the second portion is characterized by unidirectional transparency at the plurality of discrete wavelength channels.

The illumination source may include multiple laser sources corresponding to the plurality of discrete wavelength channels.

The illumination source may include multiple light-emitting diodes corresponding to the plurality of discrete wavelength channels.

The illumination source may include a continuous illumination source and a plurality of bandpass filters.

Receiving the design may include receiving an identifier of the design from a personal electronic device, and accessing the design from a server using the identifier.

The instructions, when executed by the one or more processors, may further cause the one or more processors to perform operations including generating a prompt for the user to apply the photochromic material.

The exposure pattern may be a first exposure pattern for face-on exposure, and the instructions, when executed by the one or more processors, may further cause the one or more processors to perform operations including defining a second exposure pattern for low-angle exposure, and exposing the surface of the face with the plurality of discrete wavelength channels in accordance with the second exposure pattern using the illumination source to impart an angular dependency as part of the cosmetic design.

The photochromic materials may be or include diarylethenes. The photochromic materials may be or include 1,2-bis(2-methyl-5-phenyl-3-thienyl)-3,3,4,4,5,5-hexafluorocyclopentene, 1,2-bis(2-methyl-5-phenyl-3-thienyl)-3,3,4,4,5,5-hexafluorocyclopentene, and 1,2-bis(3-methylbenzo(b)thiophen-2-yl)perfluorocyclopentene.

In one aspect, a method for application of cosmetic designs includes receiving, by a computer system, a numerical representation of a cosmetic design. The numerical representation includes a tensor of color intensity information for a plurality of colors, the plurality of colors corresponding to a cosmetic composition includes a mixture of photochromic materials. The method includes detecting, using a camera in electronic communication with the computer system, a user of the system facing a visible light mirror. The camera is in optical communication with the visible light mirror via a partially transparent portion of the visible light mirror. The method includes generating, using the camera, a numerical representation of a portion of a face of the user. The numerical representation of the face includes a tensor of position information defining a surface of the face. The method includes defining, by the computer system, an exposure pattern for the surface of the face, at least in part by projecting the tensor of color intensity information onto the tensor of position information. The method also includes exposing, using an illumination source in electronic communication with the computer system, the surface of the face with a plurality of discrete wavelength channels in accordance with the exposure pattern using the illumination source. The illumination source is physically coupled with the visible light mirror and configured to emit the plurality of discrete wavelength channels.

Exposing the surface of the face may include transmitting the plurality of discrete wavelength channels through the visible light mirror via the second portion.

The instructions, when executed by the one or more processors, may further cause the one or more processors to perform operations including generating a first prompt indicating a face-on posture relative to the illumination source, prior to exposing the surface of the face in accordance with the first exposure pattern, and generating a second prompt indicating a side-on posture relative to the illumination source, prior to exposing the surface of the face in accordance with the second exposure pattern.

In one aspect, a non-transitory computer readable memory stores instructions that, when executed by one or more processors of a computer system, cause the one or more processors to perform operations of the method above. The computer system may be or include the system of the preceding aspect.

Other technical features may be readily apparent to one skilled in the art from the following figures, descriptions, and claims.

BRIEF DESCRIPTION OF THE FIGURES

The foregoing aspects and many of the attendant advantages of the present disclosure will become more readily appreciated as the same become better understood by reference to the following detailed description, when taken in conjunction with the accompanying drawings.

DETAILED DESCRIPTION

Figure 1:
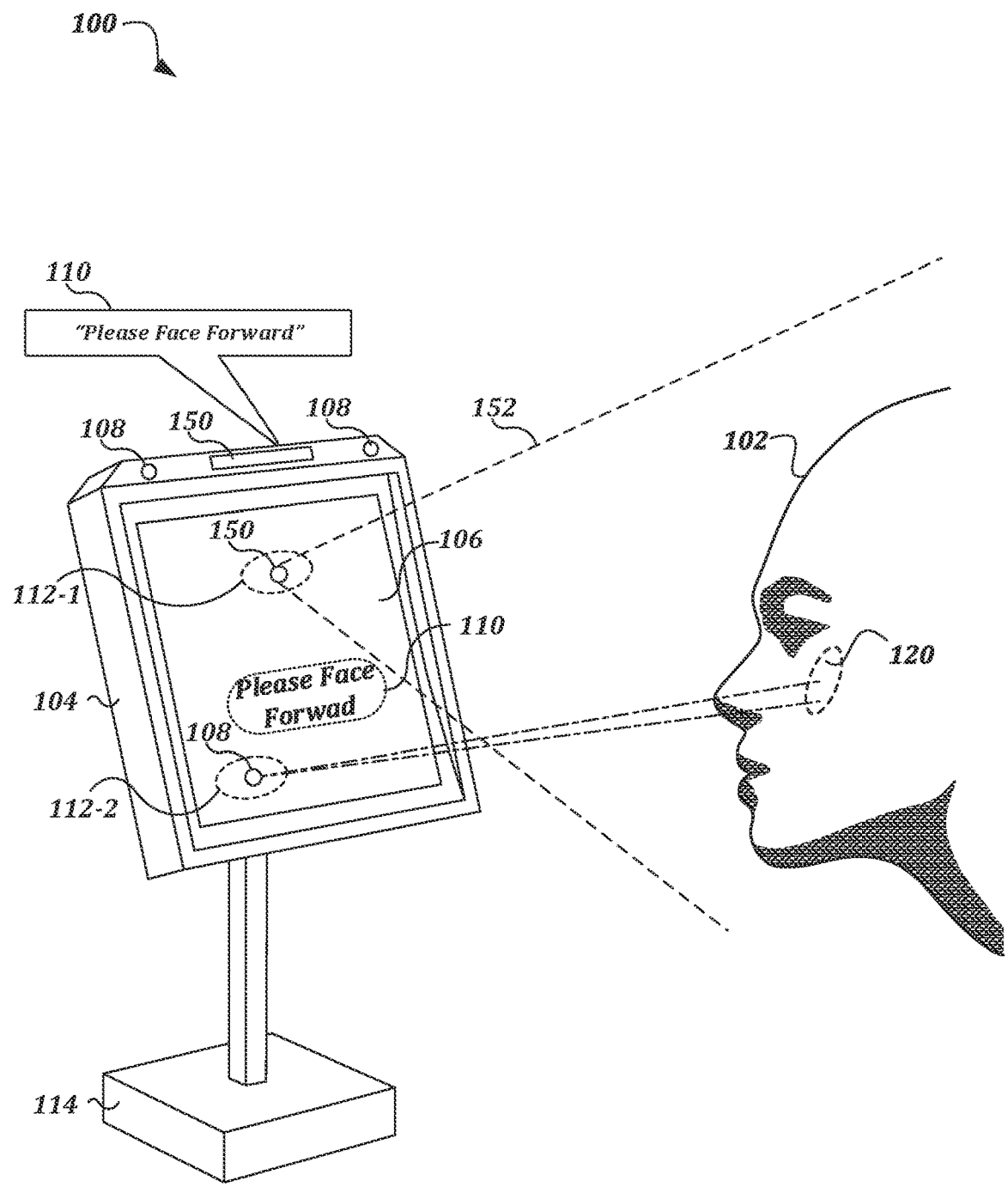
FIG. 1 is a schematic illustration of an embodiment of a system incorporating sensors and an illumination source for application of cosmetic designs, according to various aspects of the present disclosure.

Application of cosmetics and makeup can be difficult by hand. For example, intricate designs and theatrical makeup are typically applied by certified makeup professionals. Additionally, self-application can be a challenge generally for those with limited mobility. Currently, handheld tools, such as cartridge-plus-dispenser solutions, implement light-activated cosmetics guided by hand. Despite representing a technological alternative to brushes, such tools are limited by cartridge sizes, cleaning methods, inability to mix or blend colors, short battery life, and lack of location awareness. Also, by depending on a handheld device, such tools do not address accessibility concerns.

Techniques are described for applying a cosmetic design to a photochromatic formulation on a body surface, such as a subject's face or other region of interest, using one or more cameras and/or other sensors. Described embodiments use image sensors to define one or more exposure patterns mapped to the body surface using a projection of the cosmetic design onto a 3D mapping of the body surface. Described embodiments are useful in many contexts, including cosmetics or body art applications, skin feature mapping or monitoring, dermatological diagnosis or treatments, or telehealth applications. In the context of such applications, described embodiments provide precision and greater ease of use over complex manual routines.

Sensors suitable for use in described embodiments include 2-dimensional (2D) or 3-dimensional (3D) cameras, proximity sensors, or other integrated or peripheral cameras or sensors. Depth sensors are used in some embodiments to obtain 3D information about surfaces and include a range of possible hardware suitable for this purpose, including RGB or infrared stereoscopic cameras, laser or infrared LiDAR sensors, and dot projectors.

3D scans enable improved measurement of actual dimensions of a body surface and allow depth sensing, which can help to determine, for example, how far the body surface is from the camera, or detailed information about particular skin features, such as wrinkles. Reference points obtained through high-quality 3D scanning in accordance with described embodiments provides greater accuracy for determining location than traditional reference points obtained with 2D imaging, such as eyes, lips, noses, or other prominent facial features, and are particularly helpful where the region of interest is occluded.

In described embodiments, a far-field camera unit captures a target body surface at a distance that allows the body surface to be mapped and navigated. In some embodiments, the far-field camera unit includes camera hardware integrated in a mobile computing device such as a smartphone or tablet computer with corresponding image processing software. Alternatively, far-field imaging is provided by one or more external cameras in communication with a computing device.

In some embodiments, the computer system detects one or more skin features (e.g., wrinkles, blemishes, visible pores, areas of hyperpigmentation, etc.) based at least in part on the image data. In some embodiments, the computer system adds representations of such features to a map of skin features. Mapping of skin features is useful, for example, to identify changes in skin conditions (e.g., changes in moles, skin pigmentation, skin texture, etc.), which can be helpful in diagnosis of dermatological conditions or for tracking progress of a skin care regimen to improve skin tone, reduce blemishes or acne lesions, minimize the appearance of wrinkles, or for other purposes. The system is capable of working with digital 3D models obtained in different ways. In some embodiments, the digital 3D model is created based on image data and depth data captured by sensors. The mapping data can then be assembled into a 3D model with reference to the positional data obtained by the far-field sensors.

The forthcoming description focuses on embodiments of a system for applying cosmetic designs, but embodiments are not limited to cosmetic designs. In some embodiments, the systems, methods, and materials described include techniques for applying cosmetic treatments to a target body surface. The cosmetic treatments may include, but are not limited to, cosmetic treatments directed at reducing the appearance of skin lines, wrinkles, loose skin, acne, scars, or other aesthetic treatments. The cosmetic treatments may be implemented through photo-induced transformation of photo-responsive materials, such as hydrogels, polymers, or other materials characterized by a shape-change, such as expansion or contraction. Under illumination at characteristic wavelengths at one or more regions of a target body surface, the photo-responsive materials may precisely expand and/or contract a region of skin, for example to stretch loose skin and/or to shrink wrinkles. In this way, the cosmetic treatments may impart similar cosmetic benefits as treatments employing invasive methods, such as surgery or botulinum toxin injections, with less inconvenience or discomfort.

FIG. 1 is a schematic illustration of an example system 100 incorporating sensors and an illumination source for application of cosmetic designs, according to various embodiments. One or more cameras 150 of a client computing device 104 includes one or more cameras and captures images of a subject's face 102. In the example shown, the client computing device 104 is a purpose-built mobile computing device including a visible light mirror 106, one or more illumination sources 108, and one or more user interface elements 110 to prompt the subject with visual and/or auditory prompts. For example, the interface elements 110 may be or include a display electronically coupled with the computer system to generate a visual prompt (e.g., "please face forward") either in a peripheral physically coupled with the mirror 106. Additionally or alternatively, the client computing device 104 may be electronically coupled with an acoustic speaker to generate an auditory prompt. The mirror 106 may include one or more portions 112 characterized by unidirectional transparency, for example, in ultraviolet, visible, and/or infrared spectral ranges. The camera(s) 150 may be optically coupled with the visible light mirror 106 to receive visible light via a first portion 112-1, and the illumination source(s) 108 may be optically coupled with the visible light mirror 106 and configured to emit a plurality of discrete wavelength channels via a second portion 112-2 of the mirror 106. In this way, the mirror 106 may appear uniform, and the system 100 may appear aesthetically as an ordinary cosmetic mirror without outward indication that the system 100 incorporates electronics, cameras 150, or illumination sources 108. For example, the components of the client computing device 104 may be integrated into a housing 114 that appears similar to a consumer cosmetic mirror rather than an electronics system. In this example, the housing 114 may conceal power sources, heat management systems, and other components described in reference to the forthcoming FIGS. 5-7.

While the client computing device 104 is illustrated in a particular configuration (e.g., as a countertop mirror or vanity mirror), additional and/or alternative form factors are contemplated. For example, the system 100 may include a smartphone or tablet computer in communication with the client computing device 104, such that one or more computer-executable operations are undertaken by the smartphone or tablet computer rather than by the client computing device 104. In this way, the client computing device 104 may be or include smaller housings 114, including, but not limited to, a cosmetics compact or an electronic peripheral configured to electronically couple with a smartphone or tablet computer that includes the camera 150, the illumination source(s) 108, or both. Similarly, the mirror 106 can be or include a full-size wall mirror, such that the client computing device 104, the camera(s) 150 and the illumination source(s) 108 may be positioned behind the mirror 106 and the one or more portions 112 may be located relative to the camera(s) 150 and the illumination source(s) 108. In such a configuration, the system 100 may be installed as a fixture, rather than as a portable system and a single mirror 106 may be configured to conceal multiple client computing devices 104, multiple cameras 150, and multiple illumination sources 108, corresponding to a number of "makeup stations," as in a salon or makeup trailer.

The illumination source 108 may include one or more optics configured to form a beam and to scan the beam. The optics may include lenses or mirrors internal to the housing 114 that may be actuated or otherwise controlled to direct a beam from the illumination source(s) 108 to the subject's face 102 and/or the region of interest 120. For example, the illumination source 108 may be or include one or more laser sources corresponding to the plurality of discrete wavelength channels, as described in more detail in reference to FIG. 3, below. In some embodiments, the illumination source 108 includes multiple light-emitting diodes corresponding to the plurality of discrete wavelength channels. Similarly, the illumination source may be or include a continuous source (e.g., a tungsten halide or broad-spectrum source) and a plurality of bandpass filters to generate the discrete wavelength channels used by the system 100 to apply a cosmetic design. In some embodiments, the illumination source 108 may be or include an image projector, configured to emit a projection of the cosmetic design onto the subject's entire face 102. In this way, the illumination source may expose the entire face of the user, and the one or more optics may include pixel arrays, filter arrays, or other addressable arrays to dynamically modulate the illumination source 108.

Figure 5:
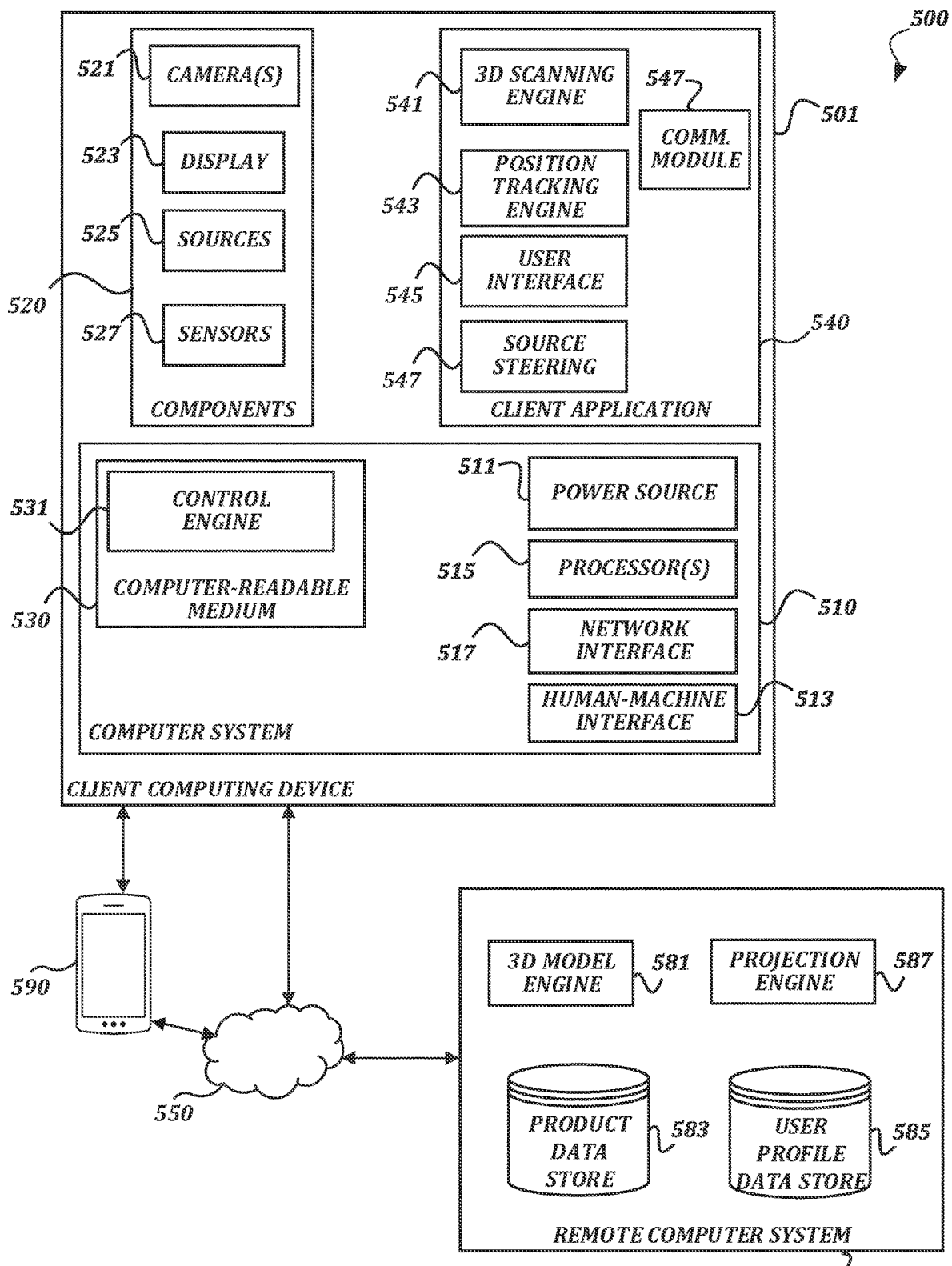
FIG. 5 is a block diagram that illustrates components included in some embodiments of a client computing device in communication with a remote computer system and a personal electronic device, in which various aspects of the present disclosure may be implemented.

As described in more detail in reference to FIG. 5, the client computing device 104 may be in electronic communication with additional systems via a network or over near-field communication protocols (e.g., wifi, bluetooth, etc.). For example, the client computing device 104 may pair with a personal electronic device, such as a smart phone or tablet, from which the client computing device 104 may receive an identifier of a design, selected for example through a browser environment presented through a smart phone. Similarly, the client computing device 104 may communicate with a server storing numerical representations of designs, and may access the design from the server. The server may be a remote server or may be a local server, where the terms "remote" and "local" are used both to refer to physical proximity to the system 100 and to denote whether the client computing device 104 and the server are configured to communicate over a public network, such as the internet or a distributed network system (e.g., a cloud system). In some cases, the client computing device 104 may store design data locally for a number of cosmetic designs, for example, using a non-transitory computer readable storage medium (e.g., SSD flash memory, hard disk drives, etc.). For example, the client computing device 104 may receive newly released cosmetic design data and associated metadata from the server, such as identifier information and interface data (e.g., images representing the cosmetic design on a model), photochromatic formulation compatibility, which may be provided via the interface elements 110 or via the mobile electronic device. In such cases, the system may be configured to operate with intermittent or no network connectivity, for example, by implementing mapping and projection software on the system itself, rather than relying on a network link with a remote server system.

In some embodiments, the camera 150 acts as a far-field camera positioned and configured to capture video or still images of subject's face 102, as well the region of interest 120 of the subject's face 102, such that the region of interest 120 is within the field of view 152 of the camera unit 150. In the example shown, the region of interest 120 is shown as a portion of the left cheek of the subject's face 102, but the region of interest 120 may cover a larger portion of the subject's face 102, such as the entirety of the subject's face 102. In some embodiments, the camera unit 150 includes more than one camera, such as for stereoscopic image or video capture and/or depth sensing. In some embodiments, the camera unit 150 also includes one or more sensors other than cameras (e.g., a LiDAR sensor or infrared dot projector for depth sensing, a proximity sensor for proximity detection, etc.). When working in conjunction with a 3D camera, these depth measurements can be mapped onto a captured 3D image. This approach is used in some embodiments to generate a 3D model of a body surface, and for real-time tracking of additional features to be used for mapping a cosmetic design onto the subject's face 102 or other body surfaces.

Figure 2A:
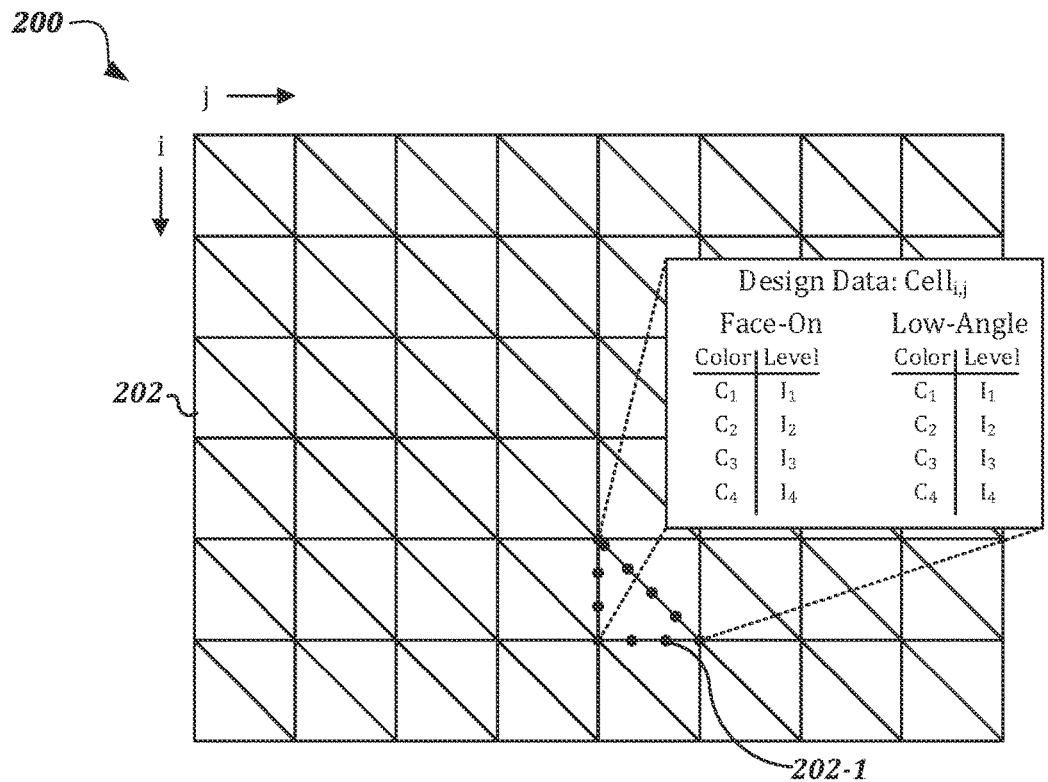
FIG. 2A is a schematic illustration of a numerical representation of a cosmetic design as a polygonal mesh including a tensor of design data in an face-on direction and a low-angle direction, according to various aspects of the present disclosure.

FIG. 2A is a schematic illustration of a numerical representation of an example cosmetic design 200 as a polygonal mesh including a tensor of design data in a face-on direction and a low-angle direction, according to various aspects of the present disclosure. The design 200 represents an exemplary visualization of a cosmetic design, including multiple polygons 202, where each polygon 202 represents a unit of the numerical representation, akin to a pixel in a digital image. Where the system implementing the processes described herein (e.g., system 100 of FIG. 1) may project the design 200 onto a surface mapping of a user's face (e.g., subject's face 102 of FIG. 1), the polygons 202 may be or include triangles or other shapes that provide greater flexibility for projection and surface mapping relative to square or rectangular pixels. That being said, the polygons 202 may be larger than the pixel size for a projector-based illumination source, such that each polygon may be defined as a number of pixels.

As shown, a first polygon 202-1 of the design 200, referenced as $Cell_{i,j}$ in the i-j plane of the numerical representation, may include multiple types of design data corresponding to different layers of the design 200. For example, the design data for the first polygon 202-1 may include, but is not limited to, a face-on color tuple and a low-angle color tuple, indicating two different colors to be generated by the system 100 at different angles. Each tuple may include color level information corresponding to the photo-responsive materials incorporated into a photochromatic formulation. For example, the photochromatic formulation may include one, two, three, four, five, or more different photo-responsive materials and three or more tuples for different angles of exposure. By selectively modulating the photo-responsive materials in accordance with the color levels for each polygon, the cosmetic design 200 may be applied to the user. As described in more detail in reference to FIG. 4, angle-dependent color may be provided using angled illumination, such that a cosmetic design may include iridescence or other angular color effects.

While each polygon 202 is illustrated as having a uniform characteristic size, it is to be understood that the polygons are representative of a tensor of color data that is referenced by cell entries in i-j space, rather than in cartesian coordinates. In this way, the first polygon 202-1 may be larger or smaller than neighboring polygons 202 when projected into a physical dimension, such as when applied to a facial mapping of a user for application of the cosmetic design 200 (e.g., region of interest 120 of the subject's face 102 of FIG. 1).

Figure 2B:
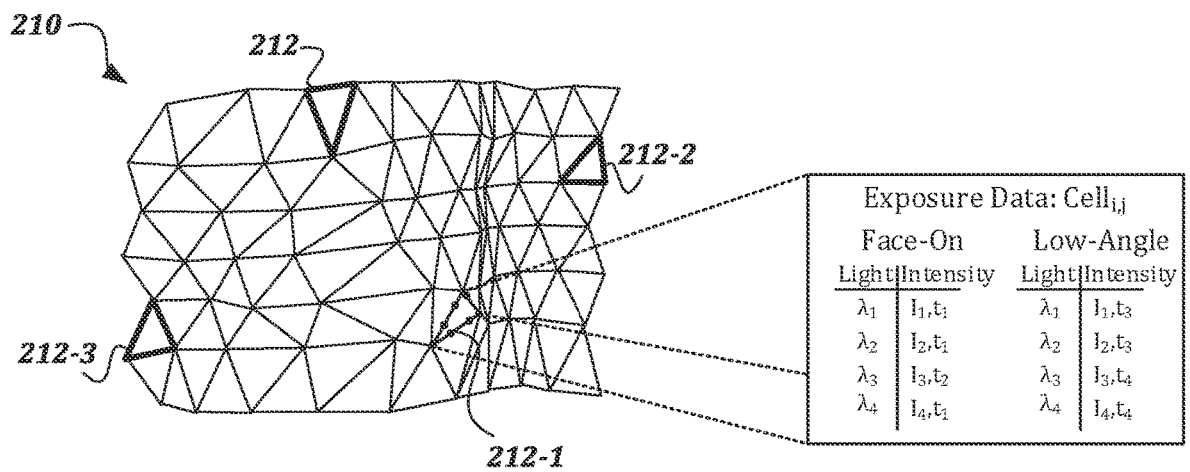
FIG. 2B is a schematic illustration of a 3-dimensional model projection of the cosmetic design onto a face mapping collected using the system of FIG. 1, according to various aspects of the present disclosure.

FIG. 2B is a schematic illustration of an example 3-dimensional projection 210 of the cosmetic design 200 onto a face mapping collected using the system of FIG. 1, according to various embodiments. As described in more detail in reference to FIG. 1, the system 100 is configured to receive the cosmetic design 200 and to generate an exposure pattern. As part of the operations of the system 100, the cosmetic design 200 may be projected onto a 3D mapping of the portion of the user's body (e.g., subject's face 102 or region of interest 120 of FIG. 1), The 3D model includes several reference points 212 in the form of corresponding triangles (although other polygon shapes are also contemplated) of a mesh structure.

Generating the 3D projection 210 may include multiple computational operations to generate a numerical representation of a portion of a face of the user using the camera (e.g., a facial mapping). The camera may be or include multiple image sensors configured to capture stereoscopic images. In this way, the numerical representation of the portion of the face may be or include a tensor of position information defining a surface of the face (e.g., in the region of interest 120 of FIG. 1). Examples of computational techniques include edge-detection, feature or point detection and tracking, and/or point-cloud methods. For example, the system 100 may be configured with a time-of-flight camera, with LiDAR systems, or with stereoscopic cameras, such that the facial mapping may represent a surface generated by contours connecting edges, points, and/or features. In some embodiments, the system 100 may include an implementation of machine learning, such as a face detection/mapping module or vSLAM system, as described in more detail in reference to FIG. 5, that may be trained to predict the facial mapping based on a subset of features and/or points measured by the camera 150. In this way, the system 100 may be configured to reduce the number of measurements used to generate the mapping, which may improve system performance, for example, by reducing the length of time used to capture images of the user's face.

Other adaptations can be performed for variations in lighting conditions, viewing angles, or other factors. As one example, a light sensor mounted on the client computing device 104 can be used to measure current lighting conditions relative to a baseline lighting condition. If the environment is too bright or too dark, the client computing device 104 may generate a prompt to increase illumination and/or may activate an illumination source (e.g., illumination source 108 of FIG. 1) that may or may not be visible to the subject (e.g., an infrared source to provide invisible illumination). In an embodiment, the client computing device 104 may provide feedback to a user (e.g., via synthesized voice cues or visual indications) to adjust the lighting conditions for better results. In some embodiments, the system may generate feedback to instruct the user to reposition relative to the camera(s) (e.g., generating a prompt to reposition the user's face from a face-on to a side-on position). It should be understood that described embodiments are capable of implementation in many possible ways to determine matches between captured image data and texture data in a 3D model, including matching detected edges or contours, color/pixel values, depth information, or the like in different combinations, and at particular threshold levels of confidence, any of which may be adjusted based on lighting conditions, user preferences, system design constraints, or other factors.

The projection 210 may reduce artifacts of applying the design to the face. For example, the polygons into which the design 200 is divided may be heterogeneously scaled, skewed, or otherwise modified when generating the projection 210, as illustrated. For example, where the cosmetic design may be described with each polygon having a uniform size, the projection 210 may include many different sizes for the polygons 212. In some embodiments, resizing may correspond to the contours of the facial mapping, where regions of high dynamic range correspond to smaller polygons 212 and regions of low dynamic range correspond to larger polygons 212. Additionally and/or alternatively, the projection 210 may be resized in accordance with information density. For example, where the number of polygons 202 making up the design 200 correspond to the resolution of the design, analogous to a pixel resolution of a digital image, information-rich regions of the design 200 may include relatively high numbers of polygons 202, compared to regions that include negligible design information. As an illustrative example, more polygons may be used to describe the regions around facial features, such as eyes, nose, mouth, or eyebrows, in contrast to regions of the cheeks, jaw, forehead, etc. In this way, the projection 210 may include exposure data for both a face-on direction (e.g., substantially normal to the surface) and for a low-angle direction, as defined for one or more angles of the user's face relative to the illumination source, using a dynamic mesh accounting for surface features.

The exposure data illustrated in FIG. 2B may be generated by taking into account the intensity values of each color channel included in the design 200, as well as exposure data for the photo-responsive materials. For example, color mixing for a first polygon 212-1, as indicated by the intensity data of the design 200, may be effected by exposing the first polygon to the multiple distinct wavelength channels (e.g., $\lambda_{1-4}$) for different intensities ("I") and durations ("t") corresponding to the characteristic activation/deactivation time of the different dies. The physical mechanisms of photochromatic materials are dynamic and sometimes may include reversible activation/deactivation, such that multiple designs 200 may be applied using a single application of photo-responsive material. In some embodiments, a "wipe" operation may be implemented by exposing the die to a neutralization wavelength.

Figure 3:
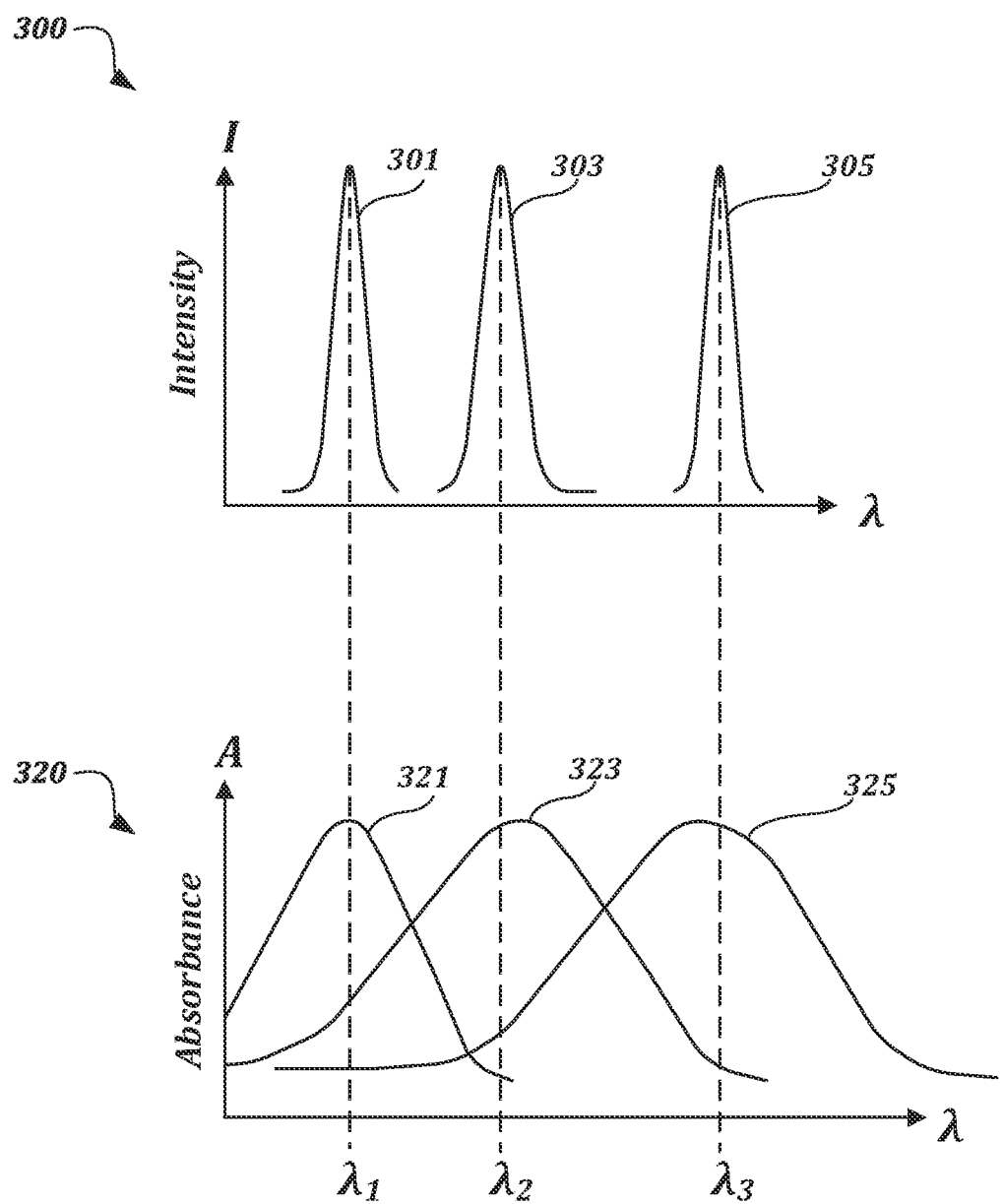
FIG. 3 describes spectroscopic aspects of the system of FIG. 1, including intensity spectra and absorbance spectra for three illumination sources and three photochromic materials, respectively, according to various aspects of the present disclosure.

FIG. 3 describes spectroscopic aspects of the system of FIG. 1, including intensity spectrum 300 and absorbance spectra 320 for three illumination sources and three photochromic materials, respectively, in accordance with various embodiments. The photochromatic formulation with which the cosmetic design (e.g., example cosmetic design 200 of FIG. 2) is implemented may be or include a blend of multiple photo-responsive and/or photochromic materials. Photochromic materials may be or include polymeric materials, polyaromatic materials, or other materials that absorb incident photons within a characteristic energy range and change electronic state as a result. The resulting change is accompanied by a predictable change in absorbance properties that is detectable as a color-change of the photochromatic formulation. Where the photochromic materials act as chemical dyes or pigments, color rendering may be optimized for a combination of chemicals that reproduce the standard CMYK color tuple, as described in terms of the cosmetic design 200 of FIG. 2. As such, the photochromatic formulation may include as many as four or more constituent photochromic materials. For example, the photochromic material may be or include diarylethenes, having a trade name DAE-X, where "X" is a number that identifies the specific photochromic material. Additionally or alternatively, the photochromatic formulation may include materials exhibiting structural color, such as inverted opals, such that activation/deactivation of the photochromic material may rely on three different materials that transition from transparent to opaque under illumination of a respective characteristic wavelength, as described in reference to the K-channel, below. In some cases, the CMY colors may produced by photochromic materials including, but not limited to, spiropyrans, spirooxazines, azobenzenes, quinones, or inorganics such as silver and zinc halides. In some embodiments, the photochromic materials may be or include DAE-0001, DAE-0012, and/or DAE-0068, although other materials are contemplated. In terms of structural formulae, the photochromic material may be or include, but is not limited to, 1,2-bis(2-methyl-5-phenyl-3-thienyl)-3,3,4,4,5, 5-hexafluorocyclopentene, 1,2-bis(2-methyl-5-phenyl-3-thienyl)-3,3,4,4,5,5-hexafluorocyclopentene, and/or 1,2-bis (3-methylbenzo(b)thiophen-2-yl)perfluorocyclopentene.

In the example spectra illustrated in FIG. 3, the intensity spectrum 300 represents the excitation or deactivation spectra of three different photochromic materials, corresponding to a CMY triad. For simplicity of explanation, the K-channel (for black color) is omitted from spectra 300 and 320. It is contemplated, however, that the K-channel may be modulated in an analogous way, using a separate activation or deactivation signal. For example, for the K-channel may be provided by including a fourth photo-responsive material in the photochromatic formulation, including, but not limited to spiropyran and/or naphthopyran. In some embodiments, the K-channel may be modulated by irradiation in the ultraviolet range, the visible range, or the infrared range.

Each constituent peak of the spectrum 300 may be generated by the illumination source of the system described in reference to FIG. 1. For example, a first emission peak 301 may be selected to correspond to a first absorbance band 321 of one of the photochromic materials. Similarly, a second emission peak 303 may be selected to correspond to a second absorbance band 323 of a second of the photochromic materials. Similarly, a third emission peak 305 may be selected to correspond to a third absorbance band 325 of a third of the photochromic materials. In this way, the illumination source (e.g., illumination source(s) 108 of FIG. 1) may be configured to expose the photochromatic formulation at or near absorbance maxima of the photochromic materials, as illustrated in absorbance spectra 320. For example, the three line sources 301, 303, and 305 of the emission spectrum 300 are aligned with three central wavelengths $\lambda_{1-3}$ for independently modulating three color channels (CMY or otherwise) as an approach to rendering a full spectrum of colors described in the cosmetic design of FIG. 2 (e.g., cosmetic design 200 of FIG. 2A). In some embodiments, the three central wavelengths may be centered between 410-475 nm, 490-540 nm, and 600-670 nm, respectively, corresponding to bluish, greenish, and reddish wavelengths of the visual spectrum, as produced by standard RGB LED triads in projection systems. In this context, the term "centered between" describes a distribution of emission intensity around a central wavelength, as determined by optical properties of the illumination source that may differ for different emission modalities. For example, a coherent line-source (e.g., a laser) may emit at a characteristic wavelength with relatively narrow wavelength distribution. By contrast, a broad-spectrum emission source, such as a blackbody source may be characterized by a wavelength distribution that is determined by a passband of a filter used to select a given center wavelength. In some embodiments, the center wavelengths may be in the ultraviolet spectral range less than 400 nm or in the NIR or IR ranges, longer than 750 nm.

Figure 4:
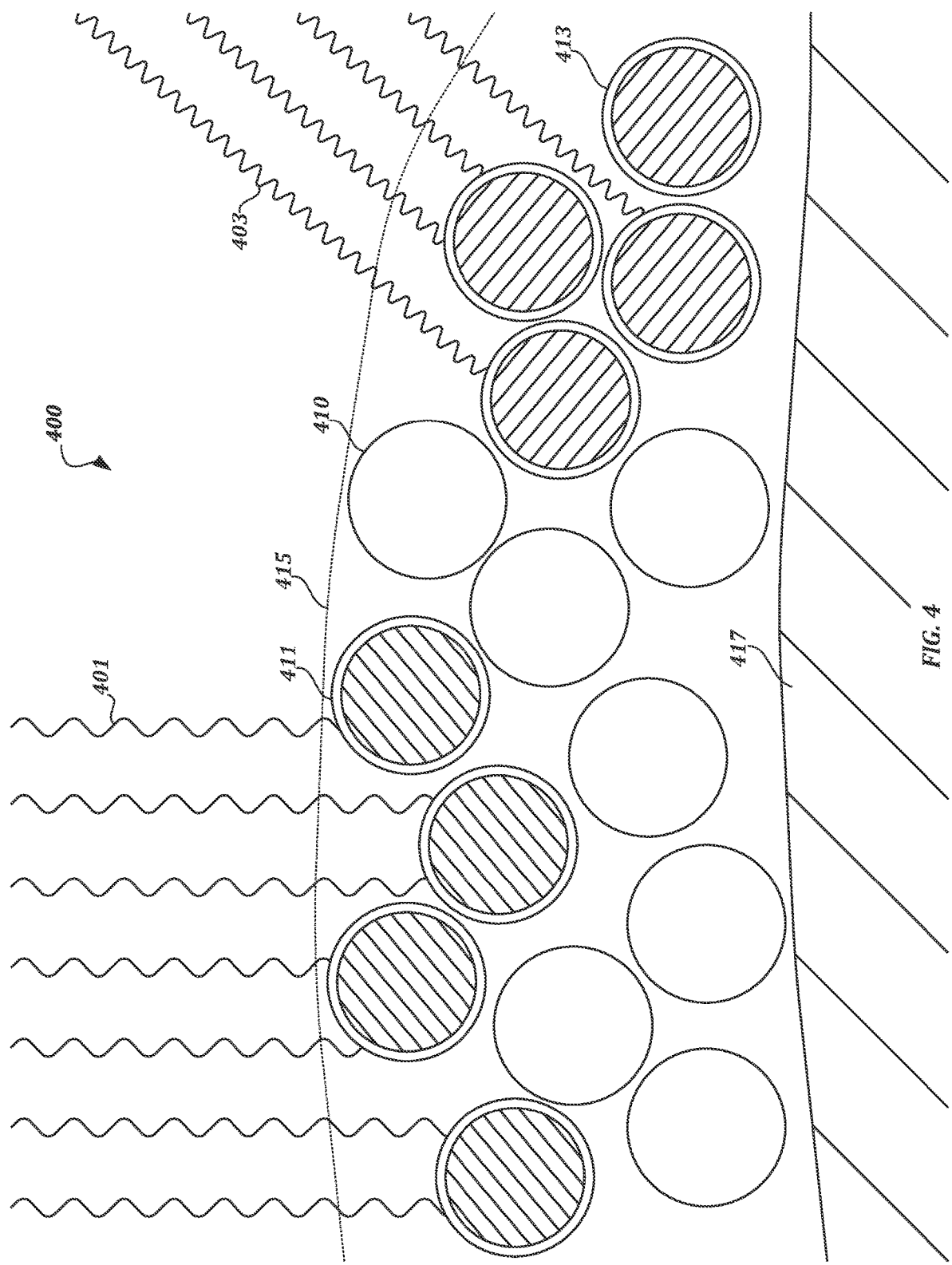
FIG. 4 is a schematic illustration of a cosmetic formulation under face-on illumination and under low-angle illumination using the system of FIG. 1 to produce polychromatic designs.

FIG. 4 is a schematic illustration of a photochromatic formulation 400 under face-on illumination 401 and under low-angle illumination 403 using the system of FIG. 1 to produce polychromatic designs, in accordance with various embodiments. As illustrated, the photochromatic formulation 400 includes a plurality of particulate photochromic materials 410 in various color-states as modulated by the illumination source (e.g., illumination source 108 of FIG. 1). As shown, a first subset of the photochromic materials 410, exposed to the face-on illumination 401, are expressing a first color state 411, while a second subset of the photochromic materials 410, exposed to the low-angle illumination 403, are expressing a second color state 413.

As illustrated, the photochromatic formulation 400 may be or include a photo-responsive powder including a blend of photochromic materials, as described in reference to FIG. 3. Additionally or alternatively, the photochromatic formulation 400 may further include a matrix material 415, such as a neutral cream or ointment that is transparent to the excitation wavelengths used to modulate the photochromic materials 410. The matrix material 415 may serve to reversibly adhere the photochromic materials 410 to the surface of the skin 417 (e.g., in region of interest 120 of FIG. 1), such that the design is preserved or does not run, for example, in response to perspiration or other physiological processes. In some embodiments, the matrix material 415 may include a dispersive material, such as a metal ceramic (e.g., titanium oxide), to absorb ultraviolet energy, such that the surface of the skin 417 may be afforded additional protection or cosmetic effects (e.g., shimmer). As described in more detail in reference to FIG. 6, the face-on illumination 401 and the low-angle illumination 403 may be provided by the same illumination source by re-orienting the surface of the skin 417 relative to the illumination source. In some embodiments, the system controlling the illumination source may incorporate multiple illumination sources in multiple orientations, such that both face-on illumination 401 and low-angle illumination 403 may be provided in a single orientation.

FIG. 5 is a block diagram that illustrates an example system 500 including components of a client computing device 501 in communication with a remote computer system 580 and a personal electronic device 590, in accordance with various embodiments. System 500 illustrates an example of the system 100 of FIG. 1, in a context of associated system elements, and, as such, describes electronics and software executing operations as described in reference to FIG. 6, below. FIG. 5 depicts a non-limiting example of system elements, features and configurations; many other features and configurations are possible within the scope of the present disclosure. In the example shown in FIG. 5, the client computing device 501 (e.g., client computing device 104 of FIG. 1) includes a computer system 510, multiple components 520 for interacting with the user and for modulating the photochromatic formulation (e.g., photochromatic formulation 400 of FIG. 4), a computer-readable medium 530, and a client application 540, that may be stored as computer-executable instructions on the computer-readable medium 530, and, when executed by the computer system 510, may implement the operations described in reference to the system 100 of FIG. 1, and the operations of the method of FIG. 6, below.

The client computing device 501 incorporates subcomponents including, but not limited to, a power source 511, a human-machine interface device 513, one or more processors 515, a network interface 517, and may include the computer-readable medium 530. The power source 511 is a direct-current power source, for example, a rechargeable battery or a rectified power supply configured to connect to line-power (e.g., 110 VAC, 220 VAC, etc.). The human-machine interface (HMI) 513 may include any type of device capable of receiving user input or generating output for presentation to a user, such as a speaker for audio output, a microphone for receiving audio commands, a push-button switch, a toggle switch, a capacitive switch, a rotary switch, a slide switch, a rocker switch, or a touch screen.

The one or more processors 515 are configured to execute computer-executable instructions stored on the computer-readable medium 530. In an embodiment, the processor(s) 515 are configured to receive and transmit signals to and/or from the components 520 via a communication bus or other circuitry, for example, as part of executing the client application 540. The network interface 517 is configured to transmit and receive signals to and from the client computing device 501 (or other computing devices) on behalf of the processors 515. The network interface 517 may implement any suitable communication technology, including but not limited to short-range wireless technologies such as Bluetooth, infrared, near-field communication, and Wi-Fi; long-range wireless technologies such as WiMAX, 2G, 3G, 4G, LTE, and 5G; and wired technologies such as USB, FireWire, and Ethernet. The computer-readable medium 530 is any type of computer-readable medium on which computer-executable instructions may be stored, including but not limited to a flash memory (SSD), a ROM, an EPROM, an EEPROM, and an FPGA. The computer-readable medium 530 and the processor(s) 515 may be combined into a single device, such as an ASIC, or the computer-readable medium 530 may include a cache memory, a register, or another component of the processor 515.

In the illustrated embodiment, the computer-readable medium 530 has computer-executable instructions stored thereon that, in response to execution by one or more processors 515, cause the client computing device 501 to implement a control engine 531. The control engine 531 controls one or more aspects of the client computing device 501 in a care routine, as described above. In an embodiment, the computer-executable instructions are configured to cause the client computing device 501 to perform one or more actions such as application of a cosmetic design, or detection of a skin feature, or administration of a therapy at a precise location of the human body surface based on a mapping of the human body surface generated using the components 520. In an embodiment, the control engine 531 controls basic functions by facilitating interaction between the computer system 510 and the components 520 according to the client application 540. In an embodiment, the control engine 531 detects input from HMI 513 indicating that a cosmetic routine is to be initiated (e.g., in response to activation of a power switch or "start" button, or detection of a face in front of the mirror 106 of FIG. 1), or receives signals from the personal electronic device 590 (e.g., over a Bluetooth paired connection).

The components of the client computing device 501 may be adapted to the application or may be specific to the application of modulating photochromatic formulations to apply cosmetic designs. For example, the components 520 may include one or more cameras 521, a display 523, one or more illumination sources 525, and/or one or more sensors 527, as described in more detail in reference to FIG. 1. In some embodiments, the components 520 are arrayed around or near a visible light mirror (e.g., mirror 106 of FIG. 1). In some embodiments, the components 520 are integrated into a single device such that the client computing device 501 or at least of portion of the elements of the client computing device 501 take on the appearance of a cosmetic mirror. In this way, the camera(s) 521, the display 523, the source(s) 525 and the sensors 527 may be optically coupled with the mirror and configured to receive and/or emit light via unidirectionally transparent and/or partially transparent portions of the mirror (e.g., portions 112 of FIG. 1). In this way, the client computing device 501 may be a specialized computing device, configured to execute the client application 540 in coordination with the components 520.

In an embodiment, the client application 540 also includes and image capture/3D scanning engine 541 configured to capture and process digital images (e.g., color images, infrared images, depth images, etc.) obtained from one or more of the components 520 including but not limited to stereoscopic images, LiDAR data, or other forms of surface/depth sensing information. In an embodiment, such data are used to obtain a clean and precise 3D contour mapping of the target body surface (e.g., subject's face 102 of FIG. 1). In an embodiment, the digital images or scans are processed by the client computing device 501 and/or transmitted to the remote computer system 580 for processing in a 3D model engine 581. In an embodiment, captured image data is used in position tracking engine 543 for determining the position of features, key-points, or edges on the target body surface. In an embodiment, the position tracking engine 543 tracks the contours of the target body surface in a 3D space, for example, by implementing v-SLAM techniques. In an embodiment, position information from the position tracking engine 543 is used to generate signals to be transmitted to the control engine 531, which are used to control one or more components 520 or elements of the computer system 510 including, for example, the sources 525 or the HMI 513, according to techniques described herein.

In an embodiment, digital 3D models described herein are generated based on sensor data obtained the client computing device 501. In such an embodiment, the digital 3D models are generated by the client computing device 501 or some other computing device, such as a remote cloud computing system, or a combination thereof. In embodiment, the digital 3D models include 3D topology and texture information, which can be used for reproducing an accurate representation of a body surface, such as facial structure and skin features, as described in more detail in reference to FIG. 2.

In some embodiments, the client application 540 includes a user interface 545. In an embodiment, the user interface 545 includes interactive functionality including but not limited to graphical guides or prompts, presented via the display through the mirror to assist a user in positioning correctly relative to the mirror, tutorial videos, or animations. Visual elements of the user interface 545 may be presented via a display of the personal electronic device 590, for example, when the display 523 does not permit high resolution video playback or for touchscreen menu navigation. In an embodiment, the user interface 545 provides guidance (e.g., visual guides such as arrows or targets, progress indicators, audio/haptic feedback, synthesized speech, etc.) to guide a user under particular lighting conditions, angles, etc., in order to ensure that sufficient data is collected for use by mapping and projection engines.

The client application 540 may include a source steering module 547. The source steering module 547 may be or include computer-readable instructions (e.g., software, drivers, etc.) for translating a numerical representation of an exposure pattern into intensity and direction data to drive the sources 525. For example, while the control engine 531 may service communication between the various components of the client computing device 501, specific drive signals may be generated by the source steering module 547. As part of the operation of the source steering module 547, the client application may receive real-time data from the camera(s) 521 and sensors 527, which may be processed by the 3D scanning engine 541, the position tracking engine 543, and may used to progressively update the mapping and projection of the cosmetic design. In this way, the source steering module 547 may respond to motion of the target body surface, thereby increasing the tolerance of the client computing device for motion on the part of the user without loss of fidelity to the cosmetic design. In some embodiments, the computational resource demand for such real time scanning/tracking, may be spread across multiple devices, such as the personal electronic device 590 and the remote computer system 580, through parallelization or distribution routines.

A communication module 549 of the client application 540 may be used to prepare information for transmission to, or to receive and interpret information from other devices or systems, such as the remote computer system 580 or the personal electronic device 590. Such information may include captured digital images, scans, or video, personal care device settings, custom care routines, user preferences, user identifiers, device identifiers, or the like. In an embodiment, the client computing device 501 collects data describing execution of care routines, image data of body surfaces, or other data. In an embodiment, such data is transmitted via the network interface 517 to the personal electronic device 590 or the remote computer system 580 for further processing or storage (e.g., in a product data store 583 or user profile data store 585). The client computing device 501 may be used by a consumer, personal care professional, or some other entity to interact with other components of the system 500, such as the remote computer system 580 or personal electronic device 590. In an embodiment, the client computing device 501 is a mobile computing device such as a smartphone or a tablet computing device equipped with the components 520 and the client application 540 or provided with the components through electronic coupling with a peripheral device.

Illustrative components and functionality of the remote computer system 580 will now be described. The remote computer system 580 includes one or more server computers that implement one or more of the illustrated components, e.g., in a cloud computing arrangement. The remote computer system 580 includes a projection engine 587, the 3D model engine 581, the product data store 583, and the user profile data store 585. In an embodiment, the 3D model engine 581 uses image data (e.g., color image data, infrared image data) and depth data to generate a 3D model of the target body surface. The image data is obtained from the client computing device 501, for example, from the camera(s) 521 or the sensor(s) 527 that are integrated with or otherwise electronically coupled with client computing device 501. In an embodiment, image data and depth data associated with a user is stored in the user profile data store 585. In an embodiment, user consent is obtained prior to storing any information that is private to a user or can be used to identify a user.

In an embodiment, the mapping/projection engine 587 performs processing of data relating to a cosmetic routine, such as generating mappings of target surfaces using image/sensor data and/or generating a projection of the cosmetic designs routine, which can then be transmitted to the client computing device 501 and/or the personal electronic device 590. The cosmetic routine information may include, for example, programmatic exposure pattern instructions for illuminating the target body surface (e.g., region of interest 120 of FIG. 1) that may be provided as instructions to be executed by the control engine 531, by the client application 540, or by the sources 525 directly. In some embodiments, the projection engine 587 generates projection/exposure data using user information from the user profile data store 585, the product data store 583, the 3D model engine 581, or some other source or combination of sources. The care projection engine 581 may employ machine learning or artificial intelligence techniques (e.g., template matching, feature extraction and matching, classification, artificial neural networks, deep learning architectures, genetic algorithms, or the like). For example, to generate multiple exposure profiles, the projection engine 587 analyze a facial mapping generated by the 3D model engine 581 to measure or map wrinkles, pigmentation, skin texture, etc., of the target body surface (e.g., subject's face 102 of FIG. 1). The projection engine 587 may receive data describing the photochromatic formulation (e.g., formulation 400 of FIG. 4), including excitation wavelengths, activation/deactivation kinetic data, and other data, for example, based on an identifier code provided by the user through the personal electronic device 590, or directly from the client computing device 501. In such a scenario, the projection engine 587 may use such information to generate a projection of the cosmetic design (e.g., cosmetic design 200 of FIG. 2) onto the target body surface, specific to the components 520 and the formulation.

The devices shown in FIG. 5 may communicate with each other via a network 550, which may include any suitable communication technology including but not limited to wired technologies such as DSL, Ethernet, fiber optic, USB, and Firewire; wireless technologies such as WiFi, WiMAX, 3G, 4G, LTE, 5G, and Bluetooth; and the Internet. In general, communication between computing devices or components of FIG. 5, or other components or computing devices used in accordance with described embodiments, occur directly or through intermediate components or devices.

Many alternatives to the arrangements disclosed and described with reference to FIGS. 1 and 5, are possible. For example, functionality described as being implemented in multiple components may instead be consolidated into a single component, or functionality described as being implemented in a single component may be implemented in multiple illustrated components, or in other components that are not shown in FIG. 1 or 5. As another example, devices in FIGS. 1 and 5 that are illustrated as including particular components may instead include more components, fewer components, or different components without departing from the scope of described embodiments. As another example, functionality that is described as being performed by a particular device or subcomponent may instead be performed by one or more other devices within a system. As an example, the 3D model engine 514 may be implemented in client computing device 501 or in some other device or combination of devices.

In addition to the technical benefits of described embodiments that are described elsewhere herein, numerous other technical benefits are achieved in some embodiments. For example, the system 500 allows some aspects of the process to be conducted independently by personal care devices or client computing devices, while moving other processing burdens to the remote computer system 510 (which may be a relatively high-powered and reliable computing system), thus improving performance and preserving battery life for functionality provided by personal care devices or client computing devices.

In general, the word "engine," as used herein, refers to logic embodied in hardware or software instructions written in a programming language, such as C, C++, COBOL, JAVA™, PHP, Perl, HTML, CSS, JavaScript, VBScript, ASPX, Microsoft.NET™, and/or the like. An engine may be compiled into executable programs or written in interpreted programming languages. Software engines may be callable from other engines or from themselves. Generally, the engines described herein refer to logical modules that can be merged with other engines or divided into sub-engines. The engines can be stored in any type of computer-readable medium or computer storage device and be stored on and executed by one or more general purpose computers, thus creating a special purpose computer configured to provide the engine or the functionality thereof.

As understood by one of ordinary skill in the art, a "data store" as described herein may be any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, as described further below. One of ordinary skill in the art will recognize that separate data stores described herein may be combined into a single data store, and/or a single data store described herein may be separated into multiple data stores, without departing from the scope of the present disclosure.

Figure 6:
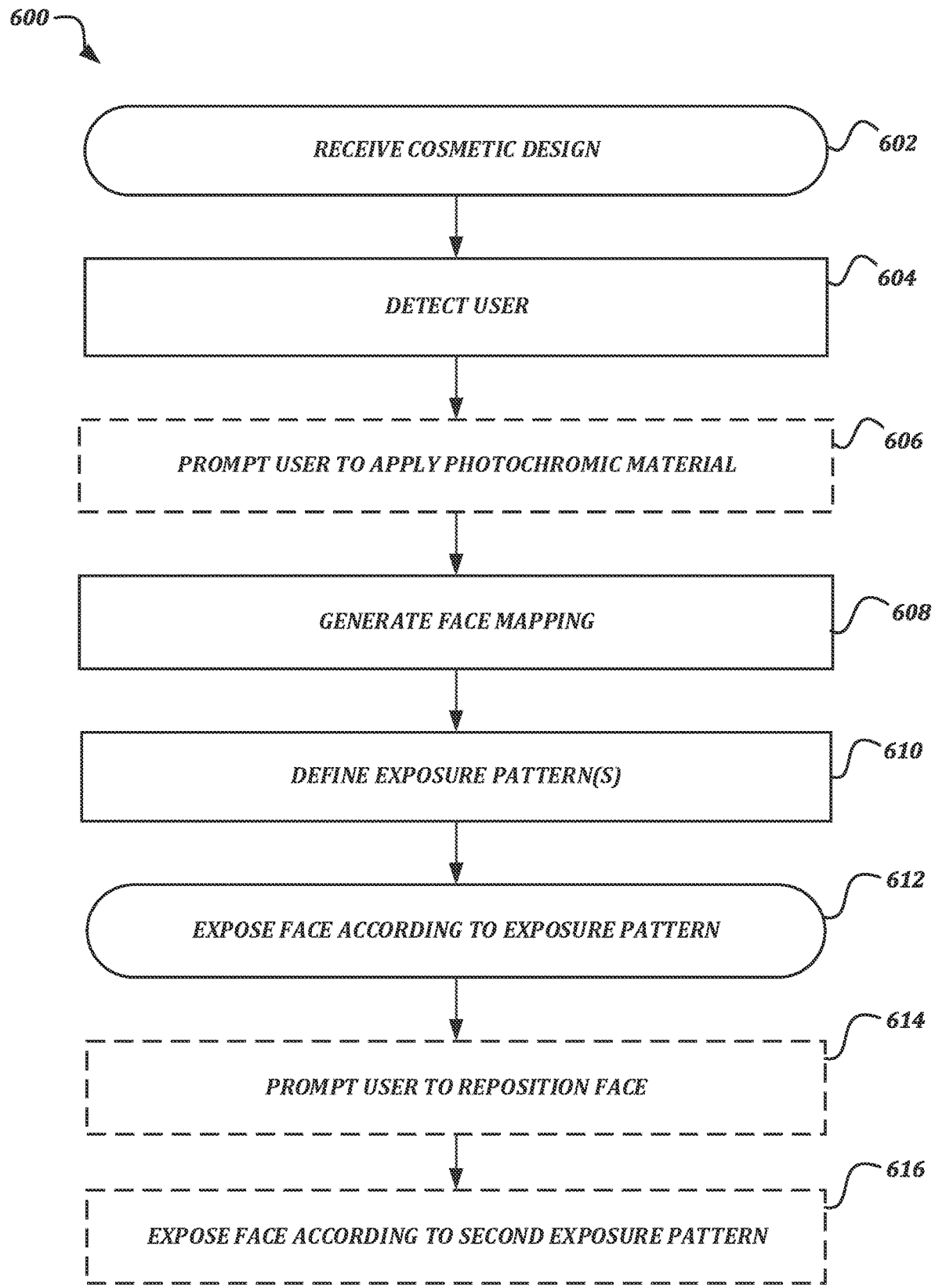
FIG. 6 is a flowchart that illustrates an example method for applying a cosmetic design on a face of a user of the system of FIG. 1, according to various aspects of the present disclosure.

FIG. 6 is a flowchart that illustrates an example method 600 for applying a cosmetic design on a user of the system of FIG. 1, in accordance with various embodiments. The example method 600 is performed by a computer system including one or more computing devices, such as client computing device 104 of FIG. 1 or client computing device 501 of FIG. 1. The example method 600 may be stored as computer-executable instructions on a computer-readable memory device. In this way, the computer system may implement the operations of example method 600 as part of executing the instructions.

At operation 602, the computer system receives a numerical representation of a cosmetic design. The numerical representation of the cosmetic design includes a tensor of color intensity information for a plurality of colors. The plurality of colors corresponds to a cosmetic composition (e.g., photochromatic formulation 400 of FIG. 4) including a mixture of photochromic materials. The computer system may receive the numerical representation of the cosmetic design (e.g., cosmetic design 200 of FIG. 2) from a user through a user interface of the computer system (e.g., HMI 513, user interface 545 of FIG. 5) or through a personal electronic device (e.g., personal electronic device 590 of FIG. 5). The numerical representation of the cosmetic design may be associated with a unique design identifier and may be retrieved from a data store (e.g., product data store 583 of FIG. 5 or computer readable medium 530 of FIG. 5), such that the tensor of color intensity information may be requested and/or retrieved by computer system in response to receiving a the unique design identifier.

At operation 604, the computer system detects, using a camera in electronic communication with the computer system, a user of the system facing a visible light mirror (e.g., mirror 106 of FIG. 1). In some embodiments, the camera is in optical communication with the visible light mirror via a partially transparent portion of the visible light mirror (e.g., first portion 112-1 of FIG. 1). In this context, detecting the user may include multiple operations included as part of face-detection and recognition routines. For example, the computer system may store feature data for a number of faces, such that the computer system is able to detect and identify the face present in the field of view of the camera (e.g., field of view 152 of FIG. 1). Such identification may benefit the system by reducing the resource demand associated with generating face mappings and projections. For example, by storing depth and image data (e.g., in user profile data store 585 of FIG. 5), the computer system may rely on periodic re-initialization for the 3D mapping operations, rather than continuous mapping, which may be more computationally intensive.

The method 600 may optionally include generating, by the computer system, a prompt for the user to apply the mixture of photochromic materials at operation 606. As described in reference to FIG. 1, prompting the user to apply the photochromatic formulation (e.g., photochromatic formulation 400 of FIG. 4) may serve as one of a number of visual/auditory guides or prompts provided to the user. Such prompts may facilitate the application of cosmetic designs, for example, where the client computing device is not equipped with a sensor (e.g., sensors 527 of FIG. 5) to detect the presence of the photochromatic formulation. In some embodiments, the photochromatic formulation includes a constituent compound or that is detectable optically. For example, a matrix (e.g., matrix material 415 of FIG. 4) may include a material that absorbs a characteristic wavelength for which the computer system is provided with a source (e.g., source(s) 525 of FIG. 5) that is typically reflected by human skin. Additionally and/or alternatively, the matrix may include a material that reflects or fluoresces under a characteristic wavelength of illumination. In this way, the optional operation 606 may be triggered in response to the computer system determining that the user has not applied the photochromatic formulation.

At operation 608, the computer system generates, using the camera, a numerical representation of a portion of a face of the user (e.g., region of interest 120 of subject's face 102 of FIG. 1). The numerical representation of the face includes a tensor of position information defining a surface of the face. The tensor of position information is described in other terms as a face-mapping or a 3D mapping of the face of the user. The computer system may implement various techniques to collect and generate depth data describing the surface to which the cosmetic design will be applied. For example, the computer system may incorporate or be electronically coupled with sensors including, but not limited to, time-of-flight cameras, stereoscopic cameras, LiDAR sensors, or point-tracking systems, to generate the numerical representation of the face. As described in more detail in reference to FIGS. 1 and 5, the numerical representation of the face may be stored in memory of the computer system and/or in separate data store (e.g., remote computer system 580 of FIG. 5) for use in generating projections of the cosmetic design onto the face mapping.

At operation 610, the computer system defines one or more exposure patterns for the surface of the face, at least in part by projecting the tensor of color intensity information onto the tensor of position information. As described in more detail in reference to FIGS. 2-4, the exposure patterns may include data for a set of characteristic wavelengths generated by the sources incorporated or in electronic communication with the computer system. For example, an exposure pattern may include spatially localized emission levels and durations for each of a map of polygons (e.g., polygons 212 of FIG. 2B) corresponding to a position on the face. In this way, the computer system may generate an exposure sequence, in terms of drive instructions for the sources, to apply the cosmetic design to the specific face of the user.

At operation 612, using an illumination source (e.g., illumination source 108 of FIG. 1) in electronic communication with the computer system, the computer system exposes a portion of the user's skin (e.g., region of interest 120 of FIG. 1) with a plurality of discrete wavelength channels. The exposure is effected in accordance with the exposure pattern. In some embodiments, the illumination source is physically coupled with the visible light mirror and configured to emit the plurality of discrete wavelength channels. In some embodiments, the illumination source is optically coupled with the mirror via a unidirectional transparent portion (e.g., second portion 112-2 of FIG. 1), such that the illumination source emits the plurality of discrete wavelength channels through the mirror via the unidirectional transparent portion. As described in more detail in reference to FIG. 5, the sources (e.g., sources 525 of FIG. 5) can be steered by the computer system as part of processing the exposure pattern into drive instructions for the sources. For example, the sources may include beam steering optics that rely on electronic actuation or dynamic lensing/optics to direct the source beam toward a specific position on the face. In some embodiments, the sources are configured to emit a field of light covering the entire surface, but with variable wavelength content at each of a number of pixels, reproducing the projected design, as described in more detail in reference to FIG. 2B. In such cases, the sources may include dynamic filters, such as programmable diffraction grating arrays or programmable filter arrays.

The method 600 may optionally include operation 614, whereby the computer system generates a second prompt for the user to reposition relative to the cameras (e.g., reposition from a face-on posture to a semi-profile posture), such that the illumination sources may be aligned with a different portion of the face. As described in more detail in reference to FIG. 4, multiple angles of exposure may impart to the photochromatic formulation an angular-color effect, such as iridescence, that is not typically available using pigment-based cosmetics. Subsequent operation 614, the method 600 may optionally include operation 616, whereby the computer system exposes the user's face according to a second exposure pattern. The second exposure pattern may include low-angle illumination, as part of applying angular or layered color to the first portion of the user's face exposed at operation 612. Similarly, operation 616 may include face-on illumination of a second portion of the user's face, such that a different region may express a color pattern according to the cosmetic design received at operation 602.

Figure 7:
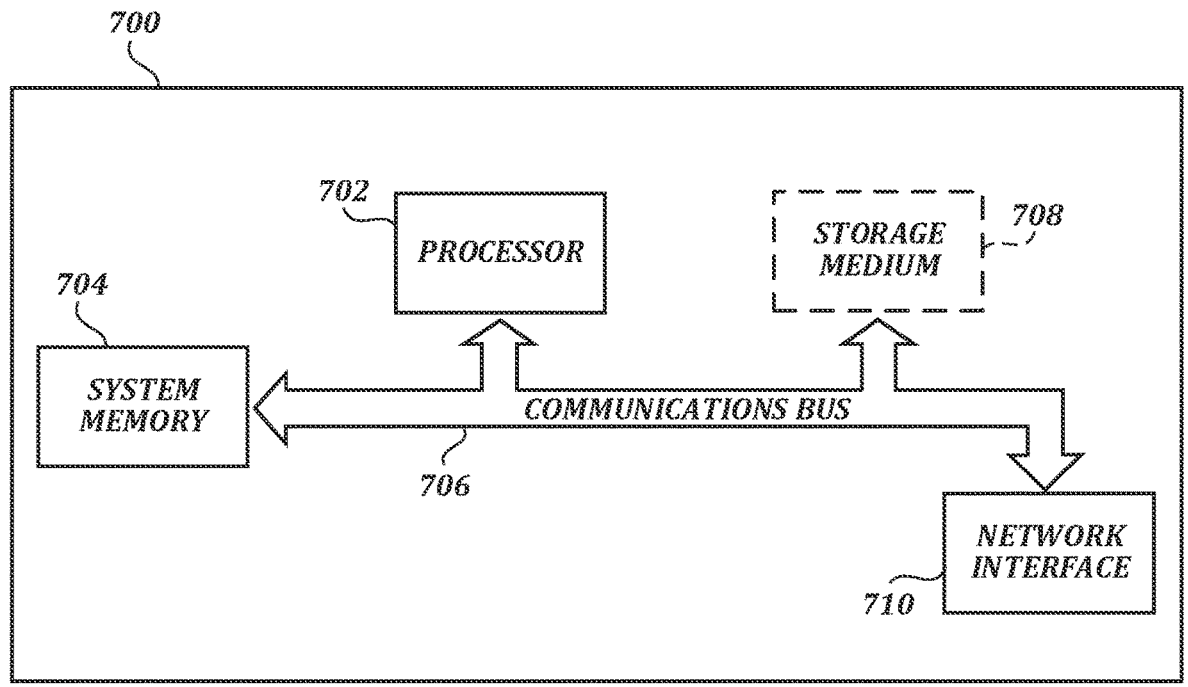
FIG. 7 is a block diagram that illustrates aspects of an illustrative computing device appropriate for use as a computing device of the present disclosure.

FIG. 7 is a block diagram that illustrates aspects of an example computing device 700, in accordance with various embodiments. While multiple different types of computing devices were discussed above, the exemplary computing device 700 describes various elements that are common to many different types of computing devices. While FIG. 7 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 700 may be any one of any number of currently available or yet to be developed devices.

In its most basic configuration, the computing device 700 includes at least one processor 702 and a system memory 704 connected by a communication bus 706. Depending on the exact configuration and type of device, the system memory 704 may be volatile or nonvolatile memory, such as read only memory ("ROM"), random access memory ("RAM"), EEPROM, flash memory, or similar memory technology. Those of ordinary skill in the art and others will recognize that system memory 704 typically stores data and/or program modules that are immediately accessible to and/or currently being operated on by the processor 702. In this regard, the processor 702 may serve as a computational center of the computing device 700 by supporting the execution of instructions.

As further illustrated in FIG. 7, the computing device 700 may include a network interface 710 comprising one or more components for communicating with other devices over a network. Embodiments of the present disclosure may access basic services that utilize the network interface 710 to perform communications using common network protocols. The network interface 710 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 710 illustrated in FIG. 7 may represent one or more wireless interfaces or physical communication interfaces described and illustrated above with respect to particular components of the system 100.

In the exemplary embodiment depicted in FIG. 7, the computing device 700 also includes a storage medium 708. However, services may be accessed using a computing device that does not include means for persisting data to a local storage medium. Therefore, the storage medium 708 depicted in FIG. 7 is represented with a dashed line to indicate that the storage medium 708 is optional. In any event, the storage medium 708 may be volatile or nonvolatile, removable or nonremovable, implemented using any technology capable of storing information including, but not limited to, a hard disk drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 704 and storage medium 708 depicted in FIG. 7 are merely examples of computer-readable media.

Suitable implementations of computing devices that include a processor 702, system memory 704, communication bus 706, storage medium 708, and network interface 710 are known and commercially available. For ease of illustration and because it is not important for an understanding of the claimed subject matter, FIG. 7 does not show some of the typical components of many computing devices. In this regard, the computing device 700 may include input devices, such as a keyboard, keypad, mouse, microphone, touch input device, touch screen, and/or the like. Such input devices may be coupled to the computing device 700 by wired or wireless connections including RF, infrared, serial, parallel, Bluetooth, Bluetooth low energy, USB, or other suitable connections protocols using wireless or physical connections. Similarly, the computing device 700 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the devices, methods, and systems described.

What is claimed is:

1. A system for application of cosmetic designs, the system comprising:
   a visible light mirror, comprising a first portion being at least partially transparent to visible light;
   a camera, optically coupled with the visible light mirror to receive visible light via the first portion;
   an illumination source, physically coupled with the visible light mirror and configured to emit a plurality of discrete wavelength channels; and
   a computer system, electronically coupled with the camera and the illumination source, and comprising one or more processors and a non-transitory computer readable storage medium storing instructions that, when executed by the one or more processors, cause the one or more processors to perform operations including:
   receiving a numerical representation of a cosmetic design, comprising a tensor of color intensity information for a plurality of colors, the plurality of colors corresponding to a photochromatic formulation comprising a mixture of photochromic materials;
   detecting a user of the system facing the visible light mirror;
   generating a numerical representation of a portion of a face of the user using the camera, the numerical representation of the face comprising a tensor of position information defining a surface of the face;
   defining an exposure pattern for the surface of the face, at least in part by projecting the tensor of color intensity information onto the tensor of position information; and
   exposing the surface of the face with the plurality of discrete wavelength channels in accordance with the exposure pattern using the illumination source.

2. The system of claim 1, wherein the camera comprises multiple image sensors, configured to capture stereoscopic images.

3. The system of claim 1, wherein the illumination source is optically coupled with the visible light mirror at a second portion of the visible light mirror, and wherein the second portion is characterized by unidirectional transparency at the plurality of discrete wavelength channels.

4. The system of claim 3, wherein exposing the surface of the face comprises transmitting the plurality of discrete wavelength channels through the visible light mirror via the second portion.

5. The system of claim 1, wherein the illumination source comprises multiple laser sources corresponding to the plurality of discrete wavelength channels.

6. The system of claim 1, wherein the illumination source comprises multiple light-emitting diodes corresponding to the plurality of discrete wavelength channels.

7. The system of claim 1, wherein the illumination source comprises a continuous illumination source and a plurality of bandpass filters.

8. The system of claim 1, wherein receiving the design comprises:
   receiving an identifier of the design from a personal electronic device; and
   and accessing the design from a server using the identifier.

9. The system of claim 1, wherein the instructions, when executed by the one or more processors, further cause the one or more processors to perform operations including generating a prompt for the user to apply the photochromic material.

10. The system of claim 1, wherein the exposure pattern is a first exposure pattern for face-on exposure, and wherein the instructions, when executed by the one or more processors, further cause the one or more processors to perform operations including:
    defining a second exposure pattern for low-angle exposure; and
    exposing the surface of the face with the plurality of discrete wavelength channels in accordance with the second exposure pattern using the illumination source to impart an angular dependency as part of the cosmetic design.

11. The system of claim 10, wherein the instructions, when executed by the one or more processors, further cause the one or more processors to perform operations including:
   generating a first prompt indicating a face-on posture relative to the illumination source, prior to exposing the surface of the face in accordance with the first exposure pattern; and
   generating a second prompt indicating a side-on posture relative to the illumination source, prior to exposing the surface of the face in accordance with the second exposure pattern.

12. The system of claim 1, wherein the photochromic materials comprise diarylethenes.

13. The system of claim 12, wherein the photochromic materials comprise 1,2-bis(2-methyl-5-phenyl-3-thienyl)-3,3,4,4,5,5-hexafluorocyclopentene, 1,2-bis(2-methyl-5-phenyl-3-thienyl)-3,3,4,4,5,5-hexafluorocyclopentene, and 1,2-bis(3-methylbenzo(b)thiophen-2-yl)perfluorocyclopentene.

14. A method for application of cosmetic designs, the method comprising:
   receiving, by a computer system, a numerical representation of a cosmetic design, comprising a tensor of color intensity information for a plurality of colors, the plurality of colors corresponding to a cosmetic composition comprising a mixture of photochromic materials;
   detecting, using a camera in electronic communication with the computer system, a user of the system facing a visible light mirror, wherein the camera is in optical communication with the visible light mirror via a partially transparent portion of the visible light mirror;
   generating, using the camera, a numerical representation of a portion of a face of the user, the numerical representation of the face comprising a tensor of position information defining a surface of the face;
   defining, by the computer system, an exposure pattern for the surface of the face, at least in part by projecting the tensor of color intensity information onto the tensor of position information; and
   exposing, using an illumination source in electronic communication with the computer system, the surface of the face with a plurality of discrete wavelength channels in accordance with the exposure pattern using the illumination source, wherein the illumination source is physically coupled with the visible light mirror and configured to emit the plurality of discrete wavelength channels.

15. A non-transitory computer readable memory, storing instructions that, when executed by one or more processors of a computer system, cause the one or more processors to perform operations of the method of claim 14.

* * * * *